US012318110B2

(12) United States Patent
Xu et al.

(10) Patent No.: US 12,318,110 B2
(45) Date of Patent: Jun. 3, 2025

(54) GREAT SAPHENOUS VEIN COLLECTION DEVICES USING DOUBLE CANNULA KNIFE

(71) Applicant: NANJING DRUM TOWER HOSPITAL, Jiangsu (CN)

(72) Inventors: Can Xu, Nanjing (CN); Dongjin Wang, Nanjing (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 0 days.

(21) Appl. No.: 18/914,014

(22) Filed: Oct. 11, 2024

(65) Prior Publication Data
US 2025/0032147 A1 Jan. 30, 2025

Related U.S. Application Data

(63) Continuation of application No. PCT/CN2023/113366, filed on Aug. 16, 2023.

(30) Foreign Application Priority Data

Sep. 6, 2022 (CN) .......................... 202211081646.8

(51) Int. Cl.
A61B 17/3205 (2006.01)
A61B 17/00 (2006.01)
(52) U.S. Cl.
CPC ............ A61B 17/32053 (2013.01); A61B 2017/00398 (2013.01); A61B 2017/00778 (2013.01)
(58) Field of Classification Search
CPC ........ A61B 17/32053; A61B 17/32002; A61B 17/3207; A61B 17/320758;
(Continued)

(56) References Cited

U.S. PATENT DOCUMENTS 5,019,089 A * 5/1991 Farr .................. A61M 25/0113
606/159
2002/0095174 A1 7/2002 Tsugita et al.
(Continued)

FOREIGN PATENT DOCUMENTS

CN 107582110 A 1/2018
CN 107981917 A 5/2018
(Continued)

OTHER PUBLICATIONS

International Search Report in PCT/CN2023/113366 mailed on Nov. 14, 2023, 6 pages.
(Continued)

Primary Examiner — Sarah A Long
(74) Attorney, Agent, or Firm — PORUS IP LLC

(57) ABSTRACT

A great saphenous vein collection device using a double-sleeve knife, including a grip, a sleeve cutting knife, and a protective sleeve is disclosed. The protective sleeve is provided inside the sleeve cutting knife and the sleeve cutting knife is rotationally connected to the protective sleeve; the protective sleeve penetrates through the grip; the grip is provided with a drive mechanism for driving the sleeve cutting knife to move relative to the grip; a threading cylinder is fixedly mounted at a top of the grip, one end of the protective sleeve is extending into an interior of the threading cylinder, a first fixing mechanism for fixing a guiding wire is provided in the interior of the threading cylinder; a first support rod is fixedly connected to a side wall of the threading cylinder, and a second support rod is fixedly connected to an end of the first support rod; the second support rod is provided with a second fixing mechanism for fixing the guiding wire at an end of the second support rod away from the first support rod.

4 Claims, 10 Drawing Sheets

(58) Field of Classification Search
CPC ........... A61B 2017/00398; A61B 2017/00778; A61B 2017/320024; A61B 2017/320032; A61B 2017/22038; A61M 25/09041; A61M 2025/09125
See application file for complete search history.

(56) References Cited

U.S. PATENT DOCUMENTS

2005/0004586 A1    1/2005  Suval
2019/0343551 A1*  11/2019  Wasdyke ....... A61B 17/320758

FOREIGN PATENT DOCUMENTS

| CN | 207821880 U | 9/2018 |
|----|-------------|--------|
| CN | 212281774 U | 1/2021 |
| CN | 112384160 A | 2/2021 |
| CN | 114681713 A | 7/2022 |
| CN | 115300054 A | 11/2022 |
| EP | 0820727 A2  | 1/1998 |

OTHER PUBLICATIONS

Written Opinion in PCT/CN2023/113366 mailed on Nov. 14, 2023, 7 pages.

* cited by examiner

GREAT SAPHENOUS VEIN COLLECTION DEVICES USING DOUBLE CANNULA KNIFE

CROSS-REFERENCE TO RELATED APPLICATIONS

This application is a Continuation of International Application No. PCT/CN2023/113366, filed on Aug. 16, 2023, which claims priority to Chinese patent application No. 202211081646.8, filed on Sep. 6, 2022, the contents of each of which are incorporated herein by reference in their entirety.

TECHNICAL FIELD

The present disclosure relates to a technical field of medical devices, and in particular relates to a great saphenous vein collection device using a double cannula knife.

BACKGROUND

In a bypass surgery, a bridge vessel (i.e., a target vessel) needs to be harvested from the patient's body, and nowadays saphenous vein or radial artery is usually chosen. In traditional surgery, the skin and muscle tissue needs to be completely peeled back, and the target vessels are separated from the collateral vessels under direct vision. The procedure generally involves making an incision in the patient's leg or arm the length of the target vessel, usually 20-25 cm. Patients experience high intraoperative trauma, long postoperative recovery time, high chance of infection, intense and prolonged pain, and visible scarring after recovery. Existing harvesting devices may help physicians perform minimally invasive surgery on the leg or arm, and physicians only need to make one or two small 1-2 cm incisions on the patient's leg or forearm, and then the target blood vessel may easily be removal. This manner is very minimally invasive to the patient, which can reduce the chance of infection and complications, decrease pain, shorten recovery time, and be more aesthetically pleasing.

However, when using a collection device to collect blood vessels, it is necessary to pass the guiding wire from the blood vessel to be collected first, and after fixing the ends of the guiding wire through the fixation device, the blood vessels are then separated and collected through the saphenous vein collection device. Since the collection device can not fix the guiding wire directly, the operation during the surgery needs more equipment, and the operation process is also more complicated, not easy to use.

Therefore, it is desirable to provide an improved great saphenous vein collection device using a double cannula knife to simplify the equipment and surgical procedure.

SUMMARY

One aspect of the present disclosure may provide a great saphenous vein collection device using a double cannula knife. The device may include a grip, a sleeve cutting knife, and a protective sleeve, wherein the protective sleeve is provided inside the sleeve cutting knife and the sleeve cutting knife is rotationally connected to the protective sleeve; the protective sleeve penetrates through the grip; the grip is provided with a drive mechanism for driving the sleeve cutting knife to move relative to the grip; a threading cylinder is fixedly arranged at a top of the grip, one end of the protective sleeve extends into an interior of the threading cylinder, a first fixing mechanism for fixing a guiding wire is provided in the interior of the threading cylinder; a first support rod is fixedly connected to a side wall of the threading cylinder, and a second support rod is fixedly connected to an end of the first support rod; and pport bar is provided with a second fixing mechanism for fixing the guiding wire at an end of the second support rod away from the first support rod.

In some embodiments, a sliding sleeve is slidably arranged on the second support rod, and the sliding sleeve is fixedly connected with a fixing plate; and the fixing plate is provided with a threading hole.

In some embodiments, the first fixing mechanism includes a fixing sleeve and a first traction rope; the fixing sleeve is provided in a ring shape, and the fixing sleeve is provided with an annular channel; the first traction rope is passed within the annular channel; and the first support rod is provided with an adjusting mechanism for pulling the first traction rope.

In some embodiments, the adjusting mechanism includes an adjusting cylinder; the adjusting cylinder is arranged on the first support rod, the adjusting cylinder is threaded arranged with an adjusting bolt; and the first traction rope passes through an inner cavity of the first support rod, a bottom end of the adjusting bolt is connected to an end of the first traction rope.

In some embodiments, the second fixing mechanism includes a fixing seat; the fixing seat is fixedly arranged on an end of the second support rod away from the first support rod; the fixing seat is provided with a through-hole, and the through-hole is slidably installed with a platen; a tension spring is fixedly connected to a bottom end of the platen, a bottom end of the tension spring is fixedly connected to the fixing seat; a second traction rope is fixedly connected to a top of the platen; and the second traction rope passes through an inner cavity of the second support rod and a top of the second traction rope is connected to a bottom end of the adjusting bolt.

In some embodiments, the drive mechanism includes a threaded pipe and a nut; the threaded pipe is arranged on an outer wall of the sleeve cutting knife, an outer wall of the threaded pipe is provided with threads, and the threaded pipe is arranged inside of the grip; the nut is fixedly arranged to an interior of the grip, the threaded pipe penetrating the nut, and the threaded pipe threadedly connected to the nut; and the threaded pipe is fitted with a first gear at one end away from the nut, and the grip is provided with a drive assembly for driving the first gear to rotate.

In some embodiments, the drive assembly includes a second gear and a motor; the second gear is rotationally arranged on an inside of the grip, the second gear is meshed with the first gear; and the motor is fixedly arranged in the grip, and an output end of the motor is connected to the second gear in transmission.

In some embodiments, a limiting post is arranged inside the grip, the limiting post and the threaded pipe are set parallel to each other, and a sliding ring is slidingly arranged on the limiting post, the sliding ring is fixedly connected to an outer wall of the protective sleeve through a connecting rod.

BRIEF DESCRIPTION OF THE DRAWINGS

The present disclosure is further illustrated in terms of exemplary embodiments, and these exemplary embodiments are described in detail with reference to the drawings. These embodiments are not limitive. In these embodiments, the same number indicates the same structure, wherein.

DETAILED DESCRIPTION

Figure 1:
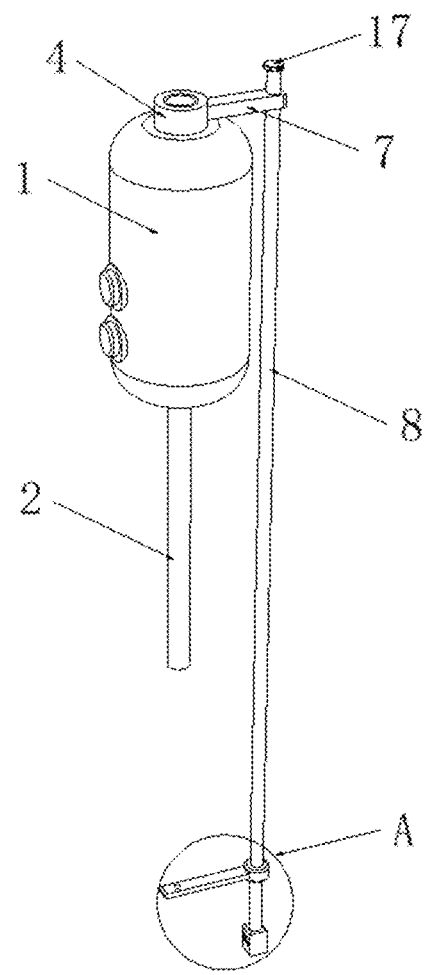
FIG. 1 is a schematic diagram of a structure of a great saphenous vein collection device using a double cannula knife according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

It will be understood that the terms "system," "device," "unit," and/or "module" used herein are one method to distinguish different components, elements, parts, sections, or assemblies of different levels in ascending order. However, the terms may be disset by other expressions if they may achieve the same purpose.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

Figure 2:
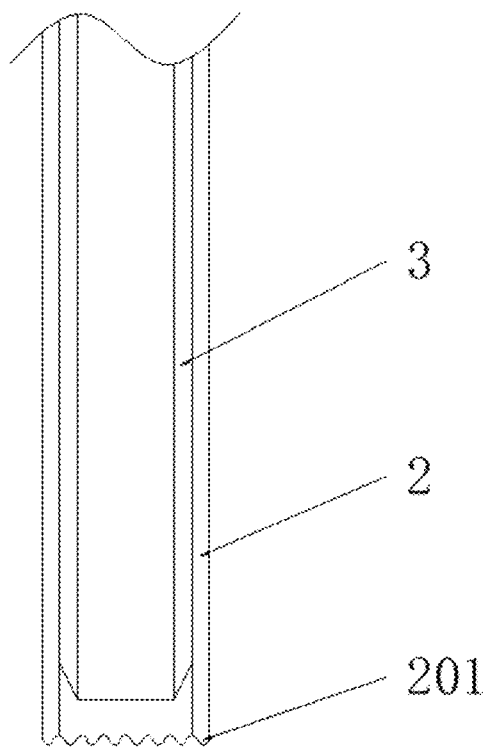
FIG. 2 is a schematic diagram of a cross-sectional structure of a cannula cutting knife according to some embodiments of the present disclosure.
Figure 3:
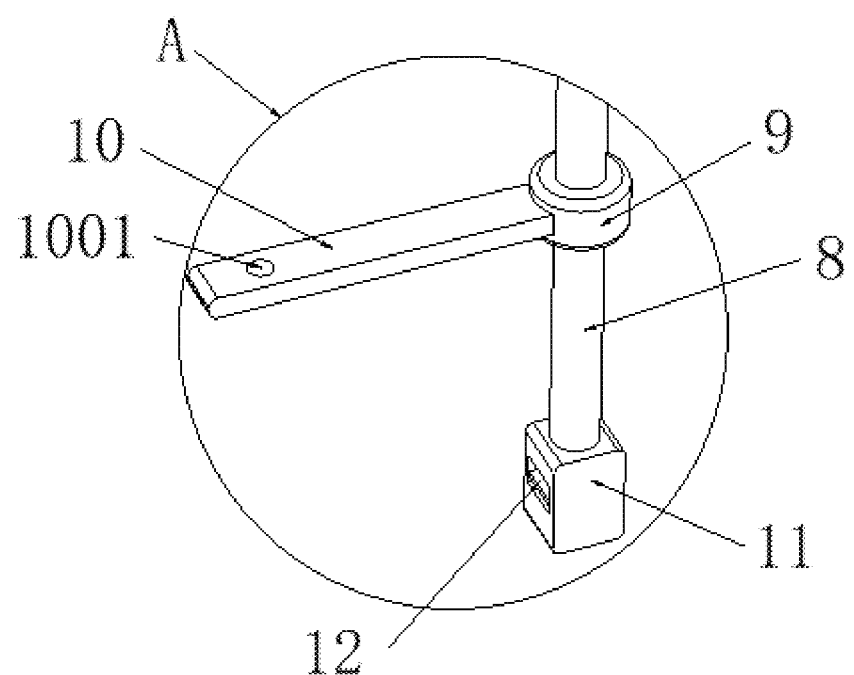
FIG. 3 is a schematic diagram of an enlarged structure at A of FIG. 1.
Figure 4:
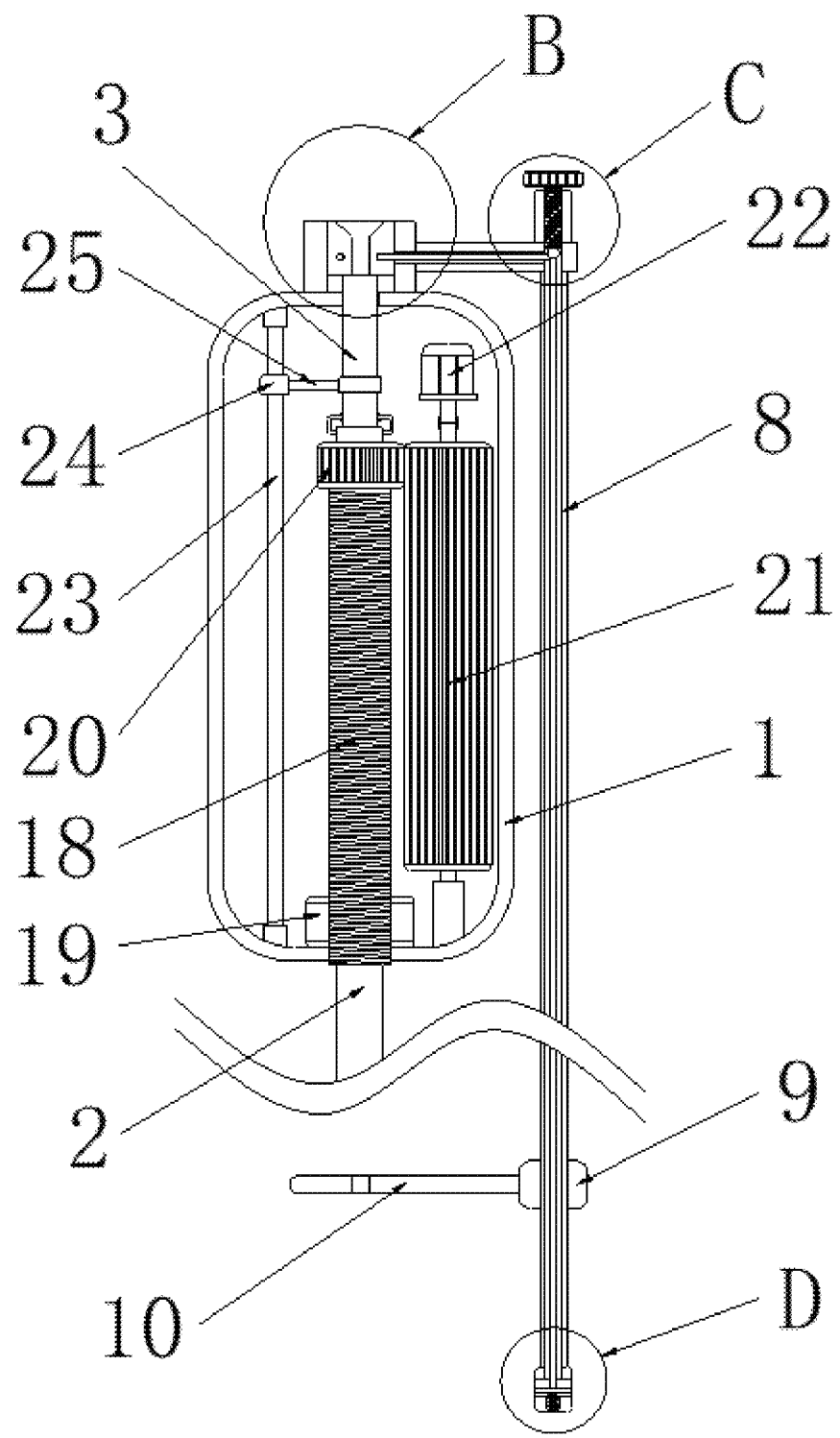
FIG. 4 is a schematic diagram of a cross-sectional structure of a great saphenous vein collection device using a double cannula knife according to some embodiments of the present disclosure.

FIG. 1 is a schematic diagram of a structure of a great saphenous vein collection device using a double cannula knife according to some embodiments of the present disclosure. FIG. 2 is a schematic diagram of a cross-sectional structure of a cannula cutting knife according to some embodiments of the present disclosure. FIG. 3 is a schematic diagram of an enlarged structure at A of FIG. 1. FIG. 4 is a schematic diagram of a cross-sectional structure of a great saphenous vein collection device using a double cannula knife according to some embodiments of the present disclosure.

As shown in FIG. 1 and FIG. 4, a great saphenous vein collection device using a double cannula knife may includes a grip 1, a sleeve cutting knife 2, and a protective sleeve 3.

The grip 1 refers to a structure that a healthcare provider may hold during surgery. In some embodiments, the grip 1 may include a hollow cylindrical structure.

The protective sleeve 3 refers to a tubular structure used to provide protection for a blood vessel. In some embodiments, the protective sleeve 3 may move relative to the blood vessel so that the blood vessel extends inside the protective sleeve 3. In some embodiments, the protective sleeve 3 may be provided inside the sleeve cutting knife 2. In some embodiments, the grip 1 and the protective sleeve 3 may be made of a variety of medical materials, such as at least one of polyvinyl chloride (PVC), polyethylene (PE), polypropylene (PP), or the like.

The sleeve cutting knife 2 refers to a structure used to cut tissues. For example, the sleeve cutting knife 2 may be used to cut the tissues surrounding the blood vessel, separate the blood vessel from the surrounding tissues, or the like. In some embodiments, the sleeve cutting knife 2 may be a tubular structure, and the blood vessel may extend into an interior of the sleeve cutting knife 2.

In some embodiments, the sleeve cutting knife 2 may be rotationally connected to the protective sleeve 3. For example, the sleeve cutting knife 2 may rotate relative to the protective sleeve 3. In some embodiments, the protective sleeve 3 is not able to slide relative to the sleeve cutting knife 2, and the protective sleeve 3 and the sleeve cutting knife 2 may be synchronized to move, such as synchronized movement along a length of the blood vessel. In a process of moving, the sleeve cutting knife 2 may cut the tissues around the blood vessel, and the blood vessel that is separated from the tissues may be extended into the protective sleeve 3, avoiding the blood vessel being cut off by contact with the sleeve cutting knife 2.

In some embodiments, as shown in FIG. 2, a blade 201 is provided at an end of the sleeve cutting knife 2.

The blade 201 refers to a sheet-like shape structure. By setting the blade 201, the effectiveness of the sleeve cutting knife 2 in cutting the tissue may be enhanced. In some embodiments, the blade 201 may be provided at an end of the sleeve cutting knife 2 along a circumference of the sleeve cutting knife 2. In some embodiments, the blade 201 may be wavy, and the tissues may be cut by the blade 201 with wavy shape, which may gradually increase a depth at which the blade 201 cuts into the tissues, result in being conducive to improving the efficiency of the cutting. In some embodiments, the blade 201 may be connected to the sleeve cutting knife 2 in a variety of ways, such as at least one of integrally molded, detachable connection, or the like. For example, the detachable connection may include at least one of a snap-fit, a snap-fit, a threaded connection, or the like. In some embodiments, the sleeve cutting knife 2 and the blade 201 may be made of a variety of medical materials, such as at least one of titanium, stainless steel, or the like.

In some embodiments, the protective sleeve 3 may penetrate through the grip 1. In some embodiments, the grip 1 may be arranged with a driving mechanism for driving the sleeve cutting knife 2 to move relative to the grip 1.

The drive mechanism may be used to output power to drive the sleeve cutting knife 2 and the protective sleeve 3 in synchronized movement. In some embodiments, the drive mechanism may include a variety of structures, such as at least one of a cylinder, a hydraulic cylinder, a geared drive chain, or the like.

In some embodiments, as shown in FIG. 1, a threading cylinder 4 is fixedly arranged at a top of the grip 1.

The threading cylinder 4 refers to a structure for guiding a guiding wire into the blood vessel. In some embodiments, the threading cylinder 4 is provided with at least one through-hole through which the guiding wire 26 (see FIG. 9) can pass. In some embodiments, the through-hole in the threading cylinder 4 may communicate with the protective sleeve 3. In some embodiments, the threading cylinder 4 may be fixedly arranged to the grip 1 in a variety of ways, such as at least one of integrally molded, threaded, bonded, or the like.

The guiding wire 26 refers to a structure for guiding the movement of sleeve cutting knife 2. In some embodiments, the guiding wire 26 may pass through at least a portion of the blood vessel, and the sleeve cutting knife 2 may be moved along a length direction of the guiding wire 26, thereby cutting the tissues that the sleeve cutting knife 2 contacts in a travel path. In some embodiments, the guiding wire 26 may be made of a variety of medical materials, such as at least one of PVC, titanium, stainless steel, or the like.

In some embodiments, one end of the protective sleeve 3 may extend into an interior of the threading cylinder 4. In some embodiments, a positioning hole adapted to fit the protective sleeve 3 may be provided within the threading cylinder 4. Positioning the protective sleeve 3 by the positioning holes is conducive to facilitating the alignment of the guiding wire 26 with the protective sleeve 3.

In some embodiments, the threading cylinder 4 is provided with a first fixing mechanism for fixing the guiding wire 26. In some embodiments, the first fixing mechanism may fix an end of the guiding wire 26 close to the threading cylinder 4, which can improve the stability of the guiding wire 26 and enhance the guiding effect of the guiding wire 26 to the sleeve cutting knife 2 during the surgery.

In some embodiments, during the surgery, the healthcare provider may incise the skin and cut the veins at the skin at both ends of the vein to be taken firstly, and the veins at the reserved end are ligated. Then, the guiding wire 26 for guiding is threaded from an end of the protective sleeve 3 close to the threading cylinder 4 and out from the other end of the protective sleeve 3. The guiding wire 26 is then threaded into the vein through the skin incision in one place, and then guided out through the skin incision in the other place. The end of the guiding wire 26 disposed within the threading cylinder 4 is secured by the first fixing mechanism, and then the sleeve cutting knife 2 and the protective sleeve 3 are driven by the drive mechanism to move in a direction away from the grip 1, so that the sleeve cutting knife 2 and the protective sleeve 3 are inserted into the tissue. During the movement of the sleeve cutting knife 2 and the protective sleeve 3, the sleeve cutting knife 2 may cut the tissue, separate the blood vessel from the surrounding tissue, and after separation, the blood vessel may enter into the protective sleeve 3 and remain inside the protective sleeve 3, thus protecting the blood vessel through the protective sleeve 3 and preventing the sleeve cutting knife 2 from cutting into the blood vessel. By fixing the one end of the guiding wire 26 in the threading cylinder 4 by the first fixing mechanism, the guiding wire 26 may not move relative to the protective sleeve 3, thereby enabling the guiding wire 26 to better position during the movement of the sleeve cutting knife 2, making the movement of the sleeve cutting knife 2 more accurate when the sleeve cutting knife 2 cuts the tissue, further preventing accidental injury to the blood vessel. By setting the first fixing mechanism, the fixation of the guiding wire 26 can be more convenient, which can reduce the difficulty of the surgical operation, and facilitate the use of the guiding wire 26.

In some embodiments, the end of the guiding wire 26 away from the threading cylinder 4 may be fixed in a variety of ways. For example, the end of the guiding wire 26 away from the threading cylinder 4 may be fixed by a second fixing mechanism, or the like. More descriptions of the second fixing mechanism can be found in following descriptions.

In some embodiments, as shown in FIG. 1, a first support rod 7 is fixedly connected to a side wall of the threading cylinder 4, and a second support rod 8 is fixedly connected to an end of the first support rod 7.

The first support rod 7 refers to a support structure for supporting the threading cylinder 4. The second support rod 8 refers to a support structure for providing support to the first support rod 7. In some embodiments, the first support rod 7 and the second support rod 8 may be in a form of a rod-like structure to reduce the space occupied by the first support rod 7 and the second support rod 8. In some embodiments, the second support rod 8 and the first support rod 7 may be provided perpendicular to each other. In some embodiments, the second support rod 8 and the grip 1 may be provided parallel to each other. In some embodiments, the first support rod 7 and/or the second support rod 8 may be hollow, which is beneficial to reduce a weight of the first support rod 7 and/or the second support rod 8, making it convenient to move and construct the first support rod 7 and the second support rod 8 during the surgery.

In some embodiments, the second support rod 8 is provided with a second fixing mechanism for fixing the guiding wire 26 at an end of the second support rod 8 away from the first support rod 7. The second fixing mechanism is capable of being used to fix an end of the guiding wire 26 away from the threading cylinder 4. By adopting the second fixing mechanism for fixing the guiding wire 26, it is possible to utilize the first fixing mechanism and the second fixing mechanism to tension the guiding wire 26, which is able to further improve the stability of the guiding wire 26 and the guiding effect of the guiding wire 26 on the sleeve cutting knife 2, thereby improving the movement accuracy of the sleeve cutting knife 2 during the surgery. In some embodiments, the guiding wire 26 is passed through a vein at one skin incision, and then guided out from another skin incision, and then the second fixing mechanism is then used to fix the end of the guiding wire 26 away from the threading cylinder 4, thereby realizing the fixation of the two ends of the guiding wire 26, and eliminating the need to fix the guiding wire 26 separately with other tools, which makes operation more convenient.

In some embodiments, the second support rod 8 and the first support rod 7 may be provided on a surgical bed, and the grip 1 may be above the surgical site. In some embodiments, the second support rod 8 may be parallel to the vein to be amputated.

In some embodiments, as shown in FIG. 3, the second support rod 8 is slidably arranged with a sliding sleeve 9, and a fixing plate 10 is fixedly connected to the sliding sleeve 9.

The sliding sleeve 9 may be used as a mounting base for mounting the fixing plate 10. The sliding sleeve 9 may drive the fixing plate 10 to move when the sliding sleeve 9 is sliding on the second support rod 8.

The fixing plate 10 may be configured to fix at least a portion of the guiding wire 26. In some embodiments, the fixing plate 10 is capable of sliding relative to the guiding wire 26 when the sliding sleeve 9 drives the fixing plate 10 to move, and during the relative sliding, the fixing plate 10 is capable of remaining in contact with at least a portion of the guiding wire 26. By making the fixing plate 10 slide relative to the guiding wire 26, the fixing plate 10 may be utilized to adjust the position of the guiding wire 26. For example, the position of the guiding wire 26 relative to an axis of the blood vessel may be adjusted, which can allow the guiding wire 26 to coincide with the axis of the blood vessel.

In some embodiments, the fixing plate 10 is provided with a threading hole 1001.

The threading hole 1001 refers to a through-hole which the guide wire 26 can pass. In some embodiments, the axis of the threading hole 1001 may be parallel to the second support rod 8. In some embodiments, the two ends of the threading hole 1001 may use rounded transitions for reducing wear and tear of the fixing plate 10 on the guiding wire 26.

In some embodiments, during the surgery, after the guiding wire 26 is led out from the skin incision, a portion of the guiding wire 26 protruding out of the skin may be passed through the threading hole 1001, and a portion of the guiding wire 26 may be in contacted with the inner wall of the threading hole 1001, and a frontal position of the guiding wire 26 may be adjusted by moving the sliding sleeve 9 until the guiding wire 26 is located in the axial position of the blood vessel.

In some embodiments, during the surgery, the healthcare provider may limit the guiding wire 26 by fixing the fixing plate 10 to a side of the skin incision away from the grip 1 via a medical tape and passing the guiding wire 26 through the threading hole 1001, and making the position the guiding wire 26 in a axial centerline position of the blood vessel. Because the fixing plate 10 may slide relative to the second support rod 8, when the grip 1, the first support rod 7, and the second support rod 8 are moved, the fixing plate 10 may always be located at the position of the skin incision, which is convenient for limiting the guiding wire 26, so that the position of the guiding wire 26 is stabilized.

Figure 5:
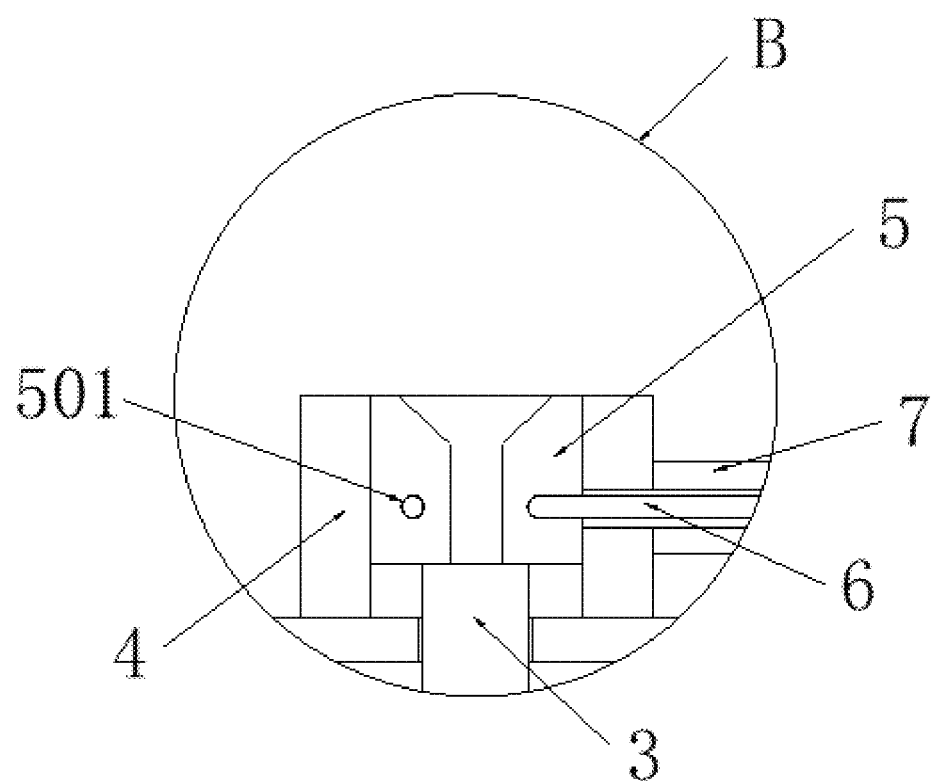
FIG. 5 is an schematic diagram of an enlarged structure at B of FIG. 4.

FIG. 5 is an schematic diagram of an enlarged structure at B of FIG. 4.

As shown in FIG. 4 and FIG. 5, the first fixing mechanism includes a fixing sleeve 5 and a first traction rope 6.

The fixing sleeve 5 refers to a structure for fixing the guiding wire 26. In some embodiments, the fixing sleeve 5 may be configured to fix at least a portion of the guiding wire 26.

In some embodiments, the fixing sleeve 5 may be arranged in conjunction with the threading cylinder 4. In some embodiments, the fixing sleeve 5 is provided in an annular shape, and the guiding wire 26 may be matingly arranged with the fixing sleeve 5. In some embodiments, the guiding wire 26 may be snapped to the fixing sleeve 5. In some embodiments, the fixing sleeve 5 is made of a resilient rubber material. In some embodiments, an annular channel 501 is opened within the fixing sleeve 5, and an axis of the annular channel 501 may be co-linear with an axis of the fixing sleeve 5. The first traction rope 6 may pass within the annular channel 501.

In some embodiments, the first traction rope 6 may be configured to apply a force to the fixing sleeve 5, such as applying a tensile force to the fixing sleeve 5 and causing the fixing sleeve 5 to tighten to clamp the guiding wire 26.

In some embodiments, one end of the first traction rope 6 is slidably connected to a body of the first traction rope 6 after passing through the annular channel 501. In some embodiments, the end of the first traction rope 6 is a closed annular structure with a variable radius, which causes an inner diameter of the closed annular structure to shrink after pulling the first traction rope 6, thereby causing the inner diameter of the fixed sleeve 5 to shrink. In some embodiments, the first support rod 7 is provided with an adjusting mechanism for pulling the first traction rope 6.

The adjusting mechanism refers to a structure used to apply a force to the first traction rope 6, such as applying a tensile force to the first traction rope 6, or the like.

Figure 6:
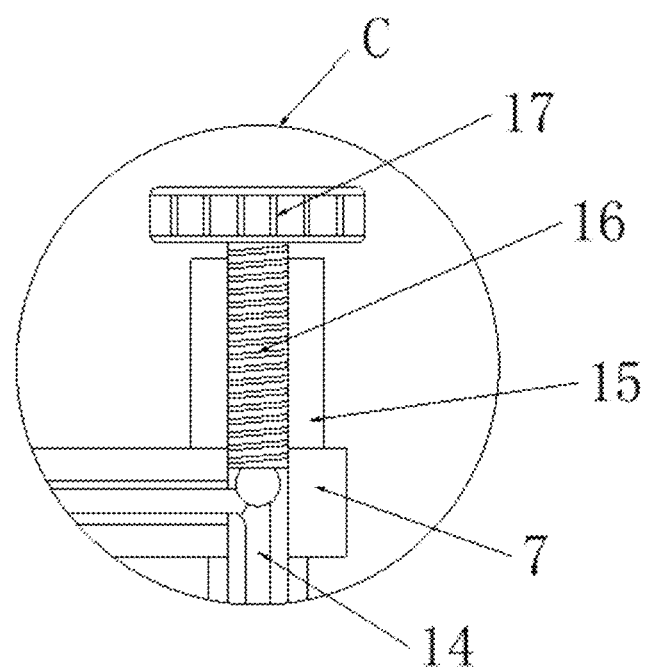
FIG. 6 is an schematic diagram of an enlarged structure at C of FIG. 4.

FIG. 6 is an schematic diagram of an enlarged structure at C of FIG. 4.

In some embodiments, as shown in FIG. 6, the adjusting mechanism may include an adjusting cylinder 15, the adjusting cylinder 15 may be fixedly arranged on the first support rod 7, and the adjusting bolt 16 may be threadedly arranged on the adjusting cylinder 15. In some embodiments, the adjusting bolt 16 may be coaxially provided with the adjusting cylinder 15.

In some embodiments, at least a portion of the first traction rope 6 may pass through an inner cavity of the first support rod 7. A bottom end of the adjusting bolt 16 may be connected to an end portion of the first traction rope 6.

In some embodiments, the bottom end of the adjusting bolt 16 may be rotationally arranged with a connecting ball, and the adjusting bolt 16 may be connected to the first traction rope 6. The connecting ball may not rotate when the adjusting bolt 16 rotates, thereby preventing the adjusting bolt 16 from rotating the first traction rope 6 when it rotates and preventing entanglement of the first traction rope 6.

In some embodiments, the adjusting bolt 17 may be fixedly arranged at a top of the adjusting bolt 16. The healthcare provider may apply a torque to the adjusting bolt 17, thereby driving the adjusting bolt 16 to rotate, which may facilitate the healthcare provider to apply the force. When the guiding wire 26 needs to be fixed, the healthcare provider may drive the adjusting bolt 16 to rotate in a direction of spinning out by the adjusting bolt 17, thereby causing the adjusting bolt 16 to move upwardly, the adjusting bolt 16 may pull the first traction rope 6 to move with the movement of the adjusting bolt 16, and an annular portion of the first traction rope 6 may pull the fixing sleeve 5 to tighten, so that the inner wall of the fixing sleeve 5 is pressed against the guiding wire 26, thereby fixing the guiding wire 26.

In some embodiments, at least one pressure sensor is provided within the fixing sleeve 5. For example, the at least one pressure sensor may be provided in the annular channel 501 of the fixing sleeve 5. In some embodiments, the pressure sensor is configured to monitor pressure change data.

The pressure change data is data related to a pressure exerted by the fixing sleeve 5 on the guiding wire 26. In some embodiments, the pressure change data may include at least one of a pressure value, a pressure difference value, or the like. The pressure value is a magnitude of the pressure exerted by the fixing sleeve 5 on the guiding wire 26 at at least one time point. The pressure difference value is a difference between pressure values corresponding to two adjacent time points. In some embodiments, the pressure change data may include at least one of a sequence comprising pressure values corresponding to a plurality of pressure sensors, a sequence comprising pressure difference values, or the like.

In some embodiments, the great saphenous vein collection device using the double cannula knife may further include a PLC controller.

The PLC controller may be used to collect, analyze, and process data, and generate control instructions based on the data, and control the device to perform corresponding functions and/or actions by issuing the control instructions. In some embodiments, the PLC controller may be communicatively connected to a pressure sensor, and the pressure sensor may upload monitored pressure change data to the PLC controller.

In some embodiments, the PLC controller may control a prompting mechanism to issue a prompt in response to the pressure change data meeting a preset pressure condition.

The preset pressure condition refers to a preset condition for triggering the prompt. In some embodiments, the preset pressure condition may include a variety. For example, the pressure value reaches a preset pressure value. When the pressure value reaches the preset pressure value, the PLC controller may determine that the adjusting bolt 16 rotates in place and the pressure exerted by the fixing sleeve 5 on the guiding wire 26 meets a surgical requirement, and it is possible to dispense with a need to rotate the adjusting bolt 16. As another example, the pressure difference value is less than a preset difference threshold. When the pressure difference value is less than the preset difference threshold, the PLC controller may determine that it is difficult for the fixing sleeve 5 to exert a greater pressure on the guiding wire 26, accordingly, it may indicate that the adjusting bolt 16 rotates in place, and the pressure exerted by the fixing sleeve 5 on the guiding wire 26 exerts a pressure that meets the surgical requirement, and there may be no need to rotate the adjusting bolt 16. In some embodiments, the PLC controller may determine the preset pressure condition in a variety of ways, such as at least one of obtaining manual input, obtaining from historical data, or the like.

The prompting mechanism is a device that may issue a prompt. The prompt is a message that may serve as a reminder. In some embodiments, the prompt may include at least one of a sound prompt, a light prompt, or the like. The prompting mechanism may include at least one of a speaker, a prompting light, or the like. In some embodiments, the prompting mechanism may be communicatively connected to a PLC controller.

The pressure sensor may monitor the pressure change data in real time, the PLC controller may analyze and process the pressure change data, and control the prompting mechanism for prompting when the pressure change data meets the preset pressure condition. When the healthcare provider adjusts the adjusting bolt and fixes the guiding wire, the prompting mechanism may play a function of automatic prompting, which can avoid a problem of loosening due to improper fixation of the guiding wire, or excessive fixation leading to abnormal loss or damage of fixing sleeve, guiding wire and other structures.

In some embodiments, the PLC controller may determine a recommended minimum value and a recommended maximum value for a rotation angle of the adjusting bolt 16 based on pressure change data at a plurality of time points, a rotation angle, and a relaxation distance based on a rotation model.

The rotation angle refers to an angle at which the adjusting bolt has turned corresponding to the pressure change data. In some embodiments, the rotation angle may be obtained in a variety of ways, such as obtained by an angle sensor provided at the adjusting bolt 16.

The relaxation distance refers to data relating to a degree tensile deformation of the first traction rope 6. The first traction rope may be stretched out after being used for a long time. After the adjusting bolt 16 drives the first traction rope 6 to move until it comes to a standstill, the first traction rope 6 may not be able to be tensioned due to the deformation, causing the the first traction rope 6 becomes loose and affects the fixing accuracy of the guiding wire 26. For example, a relaxation distance of 0.5 mm indicates that the tensile deformation degree of the first traction rope 6 is 0.5 mm, and the adjusting bolt 16 needs to pull the first traction rope 6 to move by a further 0.5 mm, to cause the first traction rope 6 to be tightened without loosening. More descriptions of the relaxation distance may be found in the following descriptions.

The recommended minimum value is a smallest angle value at which the adjusting bolt 16 needs to be turned to satisfy a condition that the fixing sleeve 5 clamps the guiding wire 26.

The recommended maximum value is a maximum angle value at which the adjusting bolt 16 needs to be turned to satisfy the condition that the fixing sleeve 5 clamps the guiding wire 26. In some embodiments, the recommended minimum value may be less than or equal to the recommended maximum value.

The rotational model is a model t used to determine the recommended minimum value and the recommended maximum value for the rotation angle of the adjusting bolt 16. In some embodiments, the rotation model may be a machine learning model such as a Neural Network (NN) model, or the like.

In some embodiments, inputs of the rotational model may include the pressure change data at the plurality of time points, the rotation angle, and the relaxation distance, and outputs may include a recommended minimum value and a recommended maximum value for the rotation angle of the adjusting bolt 16. The rotation angle may correspond to the pressure change data at the plurality of time point, and the relaxation distance may correspond to the pressure change data at the plurality of time points.

In some embodiments, the rotational model may be trained by a plurality of labeled training samples. In some embodiments, the PLC controller may acquire a training data set. The training dataset may include a plurality of training samples and a label corresponding to each training sample. In some embodiments, the PLC controller is communicatively connected to an external server. In some embodiments, the external server may perform multiple rounds of iterations. The at least one round of iteration may include selecting one or more training samples from the training data set, inputting the one or more training samples into the rotational model, obtaining a model prediction output corresponding to the one or more training samples; calculating a value of a loss function by substituting the model prediction output corresponding to the one or more training samples and the label of the one or more training sample into a formula. The PLC controller may inversely update model parameters in the rotational model based on the value of the loss function. In some embodiments, an external server may reverse update the model parameters in the rotational model in multiple ways. For example, the update may be based on gradient descent, or the like. When an iteration end condition is satisfied, the iteration is ended, and the trained and completed model is obtained. The iteration end condition may include the loss function converging, the number of iterations reaching a threshold, or the like. In some embodiments, the external server may implant the trained rotational model within the PLC controller.

In some embodiments, the training samples may include sample pressure change data, sample rotation angle, and sample relaxation distance. The labeling may include a sample recommended minimum and a sample recommended maximum corresponding to the training samples.

In some embodiments, the external server may determine the training samples based on at least one of historical experimental data, historical usage/trial data, or the like.

In some embodiments, the external server may determine the label based on at least one of historical experimental data, historical usage/trial data, or the like. For example, the historical experimental data and the historical usage/trial data may include different pressure change data monitored by the pressure sensor and the corresponding relaxation distance when the adjusting bolt is rotated. A minimum rotation angle corresponding to a lowest pressure and a maximum rotation angle corresponding to a highest pressure may be determined as labels under a condition that the guiding wire does not slip and does not cause a significant reduction in a lifespan of the fixing sleeve. In some embodiments, when the count of the minimum rotation angle and the maximum rotation angle is a plurality of numbers, respectively, the external server may take an average of the minimum rotation angles corresponding to a lowest pressure and an average of the maximum rotation angles corresponding to a highest pressure as a label.

The recommended minimum and maximum values of the rotation angle of the adjusting bolt are predicted by the rotation model, which may predict the maximum and minimum angles of the rotation of the adjusting bolt required to clamp the guiding wire with the fixing sleeve. Adjusting the adjusting bolt based on an angular range of the maximum rotation angle and the minimum rotation angle prevents over-adjustment of the adjusting bolt from deforming or damaging the guiding wire and affecting its service life, or improper adjustment of the adjusting bolt from not fixing the guiding wire in place and affecting the surgical precision. When predicting the recommended minimum value and the recommended maximum value, by considering the effect of the deformation of the first traction rope on the clamping of the guiding wire in the fixing sleeve and the relaxation distance, the accuracy of determining the recommended minimum value and the recommended maximum value is improved.

In some embodiments, as the number of use times or a use duration increases, the first traction rope 6 and/or the fixing sleeve 5 may suffer from deformations, deterioration, or the like, resulting in a gradual increase in the recommended minimum value.

In some embodiments, the PLC controller may determine, based on a standard recommended minimum value, whether to replace the first traction rope 6 and/or the fixing sleeve 5.

The standard recommended minimum value is a preset value used for comparing with the recommended minimum value. For example, when the recommended minimum value is greater than or equal to the standard recommended minimum value, it indicates that the PLC controller becomes less effective in realizing the automatic control based on the output of the rotation model, and it is necessary to replace the first traction rope and/or the fixing sleeve.

In some embodiments, the PLC controller may determine the standard recommended minimum value in a variety of ways, such as at least one of obtaining manual input, obtaining from historical data, or the like.

In some embodiments, the PLC controller may determine, based on the training samples, a magnitude of service life reduction corresponding to the sample pressure change data. The PLC controller may determine at least one sample pressure change data corresponding to the magnitude of service life reduction being greater than a predetermined magnitude threshold, and the PLC controller may calculate an average value of a sample rotational angle corresponding to the sample pressure change data, using the average value as the standard recommended minimum value.

More descriptions of the training samples may be found in above descriptions.

The magnitude of service life reduction refers to a degree to which the service life of the first traction rope 6 and/or the fixing sleeve 5 is reduced under different pressures. In some embodiments, the PLC controller may determine a magnitude threshold in a variety of ways, such as at least one of obtaining manual input, obtaining from historical data, or the like.

In some embodiments, the standard recommended minimum value may be related to the recommended maximum value. In some embodiments, the PLC controller may determine the recommended maximum value as the standard recommended minimum value. In some embodiments, the PLC controller may calculate the standard recommended minimum value based on a first predetermined algorithm. The first predetermined algorithm may include an equation:

$$T_b = T_g \times k$$

$T_b$ denotes the standard recommended minimum value, $T_g$ denotes the recommended maximum value, and k denotes a coefficient. In some embodiments, a value range of k may be from 0.9 to 1. In some embodiments, the PLC controller may determine k in a variety of ways, such as at least one of obtaining manual inputs, obtaining from historical data, or the like.

By determining the standard recommended minimum value, it is possible to determine whether the first traction rope and/or the fixing sleeve needs to be replaced based on the standard recommended minimum value. When the recommended minimum value is greater than or equal to the standard recommended minimum value, the first traction rope and/or fixing sleeve may be replaced in time, which may avoid the deformation and aging of the first traction rope and/or the fixing sleeve, causing the guiding wire not to be fixed in place and affect the precision of the surgery.

Figure 7:
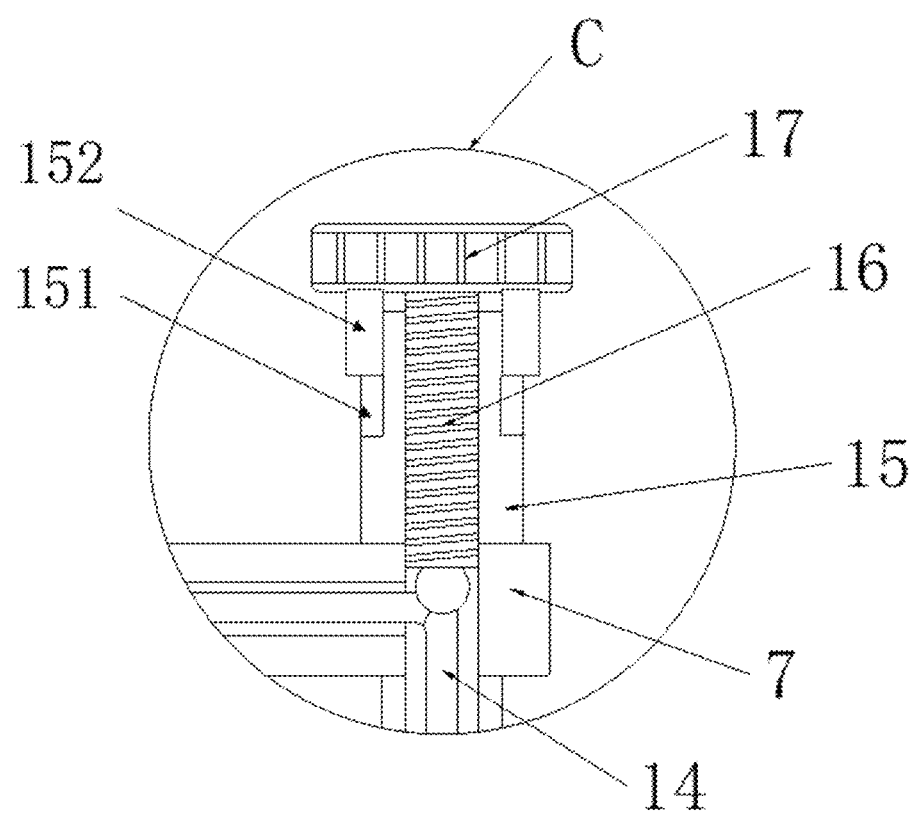
FIG. 7 is a schematic diagram of a structure of a limiting assembly according to some embodiments of the present disclosure.

FIG. 7 is a schematic diagram of a structure of a limiting assembly according to some embodiments of the present disclosure.

In some embodiments, as shown in FIG. 7, the adjusting cylinder 15 may include a limiting assembly.

The limiting assembly is a structure used to limit the adjusting bolt 16. When the adjusting bolt 16 is adjusted, the limiting assembly may be utilized to limit a movement of the adjusting bolt 16, preventing the adjusting bolt 16 from loosening and resulting in loosening of the fixing sleeve 5 from extruding the guiding wire 26.

In some embodiments, the limiting assembly may include a limiting groove 151 and a limiting block 152.

The limiting groove 151 refers to a groove-like structure provided on the adjusting cylinder 15. In some embodiments, the limiting groove 151 is provided on an outer surface of the adjusting cylinder 15. In some embodiments, the limiting groove 151 may be in a same direction as an extension of the adjusting bolt 16, i.e., the limiting groove 151 may be parallel to the axis of the adjusting bolt 16.

The limiting block 152 refers to a structure for limiting the adjusting bolt 16. In some embodiments, the limiting block 152 is slidably arranged within the limiting groove 151. In some embodiments, the limiting block 152 may be snap-fit to the adjusting bolt 17. In some embodiments, the adjusting bolt 17 is provided with a slot adapted to the limiting block 152. At least a portion of the limiting block 152 may extend into the slot. When the adjusting bolt 16 is adjusted to a position, the limiting block 152 may be slid so that the limiting block 152 snaps into the slot, thereby limiting the adjusting bolt 16.

In some embodiments, one or more limiting assemblies may be provided on the adjusting cylinder 15. The plurality of limiting assemblies may be distributed in a circular pattern around a circumference of the adjustment cylinder 15.

When the adjusting bolt is used for a long time, there may be problems such as aging, wear and tear, resulting in a gap between the adjusting bolt and the adjusting cylinder. When the adjusting bolt is adjusted to the position, it is affected by the gap, which may make the adjusting bolt fall back, loosen and other problems. By adopting the limiting assembly, the movement of the adjusting bolt may be limited after the adjusting bolt is adjusted to the position, preventing the adjusting bolt from backing out and loosening, and ensuring the clamping accuracy of the guiding wire.

In some embodiments, a limiting motor may be provided on the adjusting cylinder 15. In some embodiments, the limiting motor and the adjusting bolt 16 may be drive connected through a variety of structures, such as at least one of a gear drive chain, a belt drive chain, or the like.

In some embodiments, the limiting motor is communicatively connected to the PLC controller. In some embodiments, the PLC controller may control the limiting motor to drive the adjusting bolt 16 to rotate. In some embodiments, the limiting motor may actuate the adjusting bolt 16 to rotate based on the recommended minimum value and the recommended maximum value. For example, the angle at which the adjusting bolt 16 is rotated is made equal to at least one of the recommended minimum value, the recommended maximum value, or the like.

In some embodiments, the PLC controller may control the prompting mechanism to issue the prompt in response to the pressure change data meeting a preset pressure condition. The healthcare provider may use the limiting assembly to limit the adjusting bolt 16 in response to the prompt.

For example, after the adjusting bolt 16 is fixed, the PLC controller may determine a relaxation distance of the first traction rope based on the pressure change data. In some embodiments, the relaxation distance may be positively correlated to a difference between a pressure value at a first time point and a pressure value at a second time point. In some embodiments, the PLC controller may calculate the relaxation distance based on a second predetermined algorithm. The second predetermined algorithm may include an equation:

$$J_s = (Y_1 - Y_2) \times x$$

$J_s$ denotes the relaxation distance, $Y_1$ denotes the pressure value at the first time point, $Y_2$ denotes the pressure value at the second time point, and x denotes a relaxation factor. The first time point is earlier than the second time point. More descriptions of the relaxation distance and the pressure value may be found in above descriptions.

In some embodiments, the PLC controller may determine the relaxation factor in multiple ways, such as at least one of obtaining manual input, obtaining from historical data, or the like.

In some embodiments, the PLC controller may construct a preset table based on historical data. For example, the PLC controller may obtain a monitored historical pressure value, historical pressure change, and a measured historical relaxation distance of the first traction rope in the historical data under different pressures after fixing the adjusting bolt via the limiting assembly, and construct a preset table based on the historical pressure value, the historical pressure change, and the historical relaxation distance. In some embodiments, the PLC controller may determine, based on the pressure value at the first time point and the pressure change corresponding to the pressure value at the first time point, the same or similar historical pressure value and historical pressure change by looking up the preset table to determine a historical relaxation distance corresponding to the historical pressure value and the historical pressure change. The PLC controller may calculate a historical relaxation coefficient based on the historical relaxation distance and the historical pressure change, and determine the historical relaxation coefficient as a current relaxation coefficient.

An automatic control of the rotation of the adjusting bolt may be realized through the use of the limiting motor. When the pressure sensor detects that the pressure change data satisfies the preset pressure condition, the rotation of the adjusting bolt may be rotated automatically in a timely manner to fix the guiding wire, thus improving the efficiency of the fixation of the guiding wire. By determining the relaxation distance, it is possible to improve the accuracy of the determined recommended minimum value and recommended maximum value, thereby improving the control accuracy of the adjusting bolt, and further guaranteeing the positioning and fixing accuracy of the guiding wire.

Figure 8:
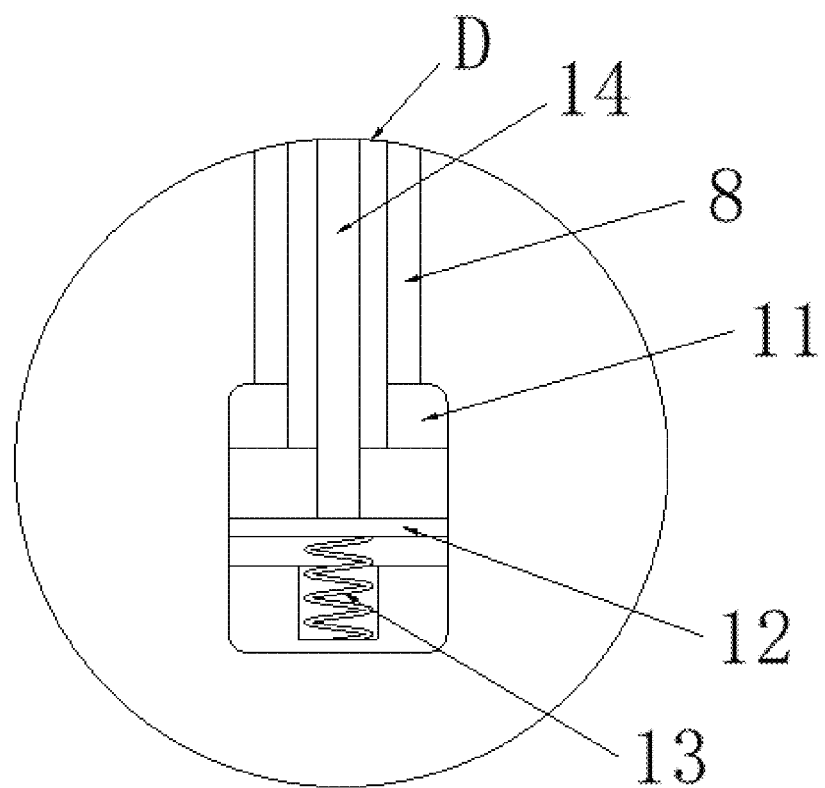
FIG. 8 is a schematic diagram of a structure at D of FIG. 4.

FIG. 8 is a schematic diagram of a structure at D of FIG. 4.

In some embodiments, as shown in FIG. 8, the second fixing mechanism includes a fixing seat 11, the fixing seat 11 is fixedly arranged at an end of the second support rod 8 away from the first support rod 7, the fixing seat 11 is provided with a through hole, and a platen 12 is slidingly arranged within the through hole, a bottom end of the platen 12 is fixedly connected to a tension spring 13, a bottom end of the tension spring 13 is fixedly connected to the fixing seat 11, and a top end of the platen 12 is fixedly connected to a second traction rope 14.

The fixing seat 11 may be used as a mounting base for mounting the platen 12 and the tension spring 13.

The platen 12 may be used to fix at least a portion of the guiding wire 26. For example, the platen 12 may squeeze at least a portion of the guiding wire 26 against an inner wall of the through-hole of the fixing seat 11.

The second traction rope 14 is a rope-like structure for applying a force to the platen 12. For example, a pulling force is exerted on the platen 12 such that the platen 12 is able to squeeze the at least a portion of the guiding wire 26. In some embodiments, the second traction rope 14 may pass through the inner cavity of the second support rod 8. In some embodiments, one end of the second traction rope 14 may be connected to a bottom end of the adjusting bolt 16, which pulls the second traction rope 14 when the adjusting bolt 16 rotates in a direction of spinning out. In some embodiments, the second traction rope 14 may be pivotally connected to a connecting ball. The connecting ball may not rotate when the adjusting bolt 16 rotates, thereby preventing the adjusting bolt 16 from rotating the second traction rope 14 when it rotates, and preventing the second traction rope 14 from tangling.

The tension spring 13 may be configured as a reset structure, and when the second traction rope 14 withdraws the force exerted on the platen 12, the tension spring 13 may be configured to the platen 12, thereby loosening the guiding wire 26.

In some embodiments, the at least a portion of the guiding wire 26 may pass through the through-hole of the fixing seat 11, and when the adjusting bolt 16 is rotated in the direction of spinning out, the at least a portion of the guiding wire 26 may drive the second traction rope 14 to move, which in turn drives the platen 12 to move, causing the guiding wire 26 to be pressed between the platen 12 and the inner wall of the through-hole, thereby fixing the end of the guiding wire 26 away from the grip 1. By connecting the first traction rope 6 and the second traction rope 14 to the adjusting bolt 17, respectively, the two ends of the guiding wire 26 may be fixed at the same time by rotating the adjusting bolt 17, which is advantageous in convenient operation.

Figure 9:
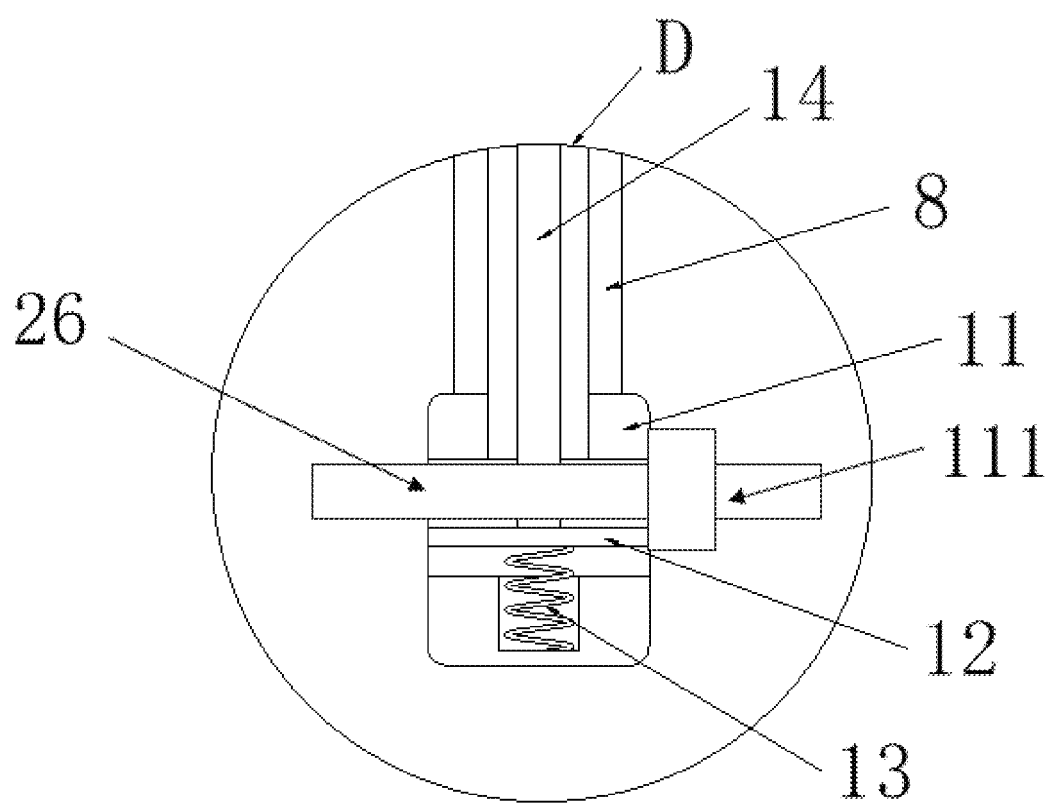
FIG. 9 is a schematic diagram of a structure of a wire guiding fixing assembly according to some embodiments of the present disclosure.

FIG. 9 is a schematic diagram of a structure of a wire guiding fixing assembly according to some embodiments of the present disclosure.

In some embodiments, as shown in FIG. 9, a guiding wire fixing assembly 111 may be provided on the fixing seat 11.

The guiding wire fixing assembly 111 may be configured to fix at least a portion of the guiding wire 26 protruding from the fixing seat 11. In some embodiments, the guiding wire fixing assembly 111 is provided with at least one through-hole. the guiding wire 26 may be threaded through the through-hole in guiding wire fixing assembly 111. In some embodiments, a diameter of the through-hole may be equal to a diameter of the guiding wire 26. In some embodiments, a portion of the guiding wire 26 that extends out of the guiding wire fixing assembly 111 may be knotted. By knotting the guiding wire 26 to form a protrusion on the guiding wire 26 with a radial dimension larger than the diameter of the guiding wire 26, the guiding wire fixing assembly 111 may be utilized to restrict movement of the protrusion, thereby fixing the guiding wire 26.

In some embodiments, the guiding wire fixing assembly 111 may be connected to the fixing seat 11 in a variety of ways, such as at least one of snap-fit, threaded connection, one-piece molding, or the like. In some embodiments, the guiding wire fixing assembly 111 may be made of an elastomeric material.

An outer surface of the guiding wire is cylindrical, and the outer surface of the guiding wire may be relatively smooth or have a smooth coating, resulting in less friction between the guiding wire and the platen, and with the fixing seat, which may result in the platen squeezing the guiding wire less effectively. By forming the protrusion on the guiding wire and utilizing the guiding wire fixing assembly to limit the movement of the protrusion, the effect of retaining the guiding wire may be improved.

In some embodiments, as shown in FIG. 4, the drive mechanism may include a threaded pipe 18 and a nut 19. In some embodiments, the threaded pipe 18 is arranged on an outer wall of the sleeve cutting knife 2.

The threaded pipe 18 refers to a tubular structure having threads. In some embodiments, the threaded pipe 18 is opened with threads on the outer wall. In some embodiments, at least a portion of the threaded pipe 18 is provided inside the grip 1. In some embodiments, the threaded pipe 18 is connected to the sleeve cutting knife 2 in a transmission way. For example, when the threaded pipe 18 is rotated and/or moved, the threaded pipe 18 may drive the sleeve cutting knife 2 to synchronize the rotation and/or movement. In some embodiments, the threaded pipe 18 and the sleeve cutting knife 2 may be connected in multiple ways, such as at least one of snap-fitting, bonding, one-piece molding, or the like.

The nut 19 refers to a structure that is capable of adapting the threads of threaded pipe 18.

In some embodiments, the nut 19 may be fixedly arranged inside the grip 1. The threaded pipe 18 may penetrate through the nut 19, and an outer wall of the threaded pipe 18 is threaded to the nut 19. When the nut 19 rotates relative to the threaded pipe 18, the nut 19 and the threaded pipe 18 may also move relative to each other simultaneously. Because the nut 19 is fixed to the grip 1, when the nut 19 is rotated relative to the threaded pipe 18 the threaded pipe 18 may move along its own axis.

In some embodiments, the end of the threaded pipe 18 away from the nut 19 is arranged with a first gear 20. In some embodiments, the threaded pipe 18 and the gear 20 may be connected in a variety of ways, such as at least one of snap-fitting, bonding, one-piece molding, or the like.

In some embodiments, a drive assembly for driving the first gear 20 to rotate is provided within the grip 1.

The drive assembly is a structure capable of outputting power. For example, an output torque may drive the first gear 20 to rotate. In some embodiments, the drive assembly may include a variety of structures, such as at least one of a gear drive chain, a worm gear drive chain, or the like. More descriptions of the drive assembly may be found in above descriptions.

In some embodiments, as shown in FIG. 3, the drive assembly may include a second gear 21 and a motor 22. The second gear 21 is rotationally arranged inside the grip 1, and the second gear 21 may mesh with the first gear 20.

The second gear 21 may be configured to rotate the first gear 20.

In some embodiments, a length of the second gear 21 is longer than a length of the first gear 20. When the first gear 20 rotates and drives the threaded pipe 18 to rotate, the threaded pipe 18 may move in an axial direction along the threaded pipe 18, and the first gear 20 may follow the threaded pipe 18 to synchronize the movement of the first gear 20. During the movement of the first gear 20, the first gear 20 may always remain engaged with the second gear 21.

The motor 22 may be configured to output power. For example, the output torque may drive the second gear 21 to rotate.

In some embodiments, the motor 22 may be fixedly arranged within the grip 1, and an output end of the motor 22 is driveably connected to the second gear 21.

In some embodiments, a button may be provided on the grip 1 and a battery may be provided within the grip 1. The battery may be electrically connected to the motor 22 via the button. The battery may be connected or disconnected to the motor 22 by controlling the button, thereby controlling the motor 22 to start or shut down. In some embodiments, the button may be provided with two buttons, wherein one of the buttons may control a forward rotation of an output end of the motor 22 and the other button may control a reverse rotation of the output end of the motor 22. When the motor 22 is turned on, the output end of the motor 22 may drive the second gear 21 to rotate, the second gear 21 may rotate to drive the first gear 20 to rotate, the first gear 20 may rotate to drive the threaded pipe 18 to rotate, and the threaded pipe 18 is threaded with the nut 19 so that the threaded pipe 18 may move relative to the grip 1 when it rotates, thereby driving the sleeve cutting knife 2 to rotate while moving relative to the grip 1, making that the sleeve cutting knife 2 cut the tissue better.

In some embodiments, as shown in FIG. 4, a limiting post 23 is fixedly arranged within the grip 1.

The limiting post 23 refers to a structure for limiting a position of the protective sleeve 3. In some embodiments, the limiting post 23 may be configured to limit a relative rotation of the protective sleeve 3 so that the protective sleeve 3 may only move and not rotate.

In some embodiments, the limiting post 23 may be arranged parallel to the threaded pipe 18. In some embodiments, the limiting post 23 is slidably arranged with a slip ring 24, which is fixedly connected to an outer wall of the protective sleeve 3 via a connecting rod 25. By the setting of the limiting post 23 and the slip ring 24, when the threaded pipe 18 is rotated, the threaded pipe 18 may transmit the torque to the sleeve cutting knife 2, which in turn transmits the torque to the protective sleeve 3, and since the protective sleeve 3 is connected to the slip ring 24 by the connecting rod 25, a rotational tendency of the protective sleeve 3 to rotate around its own axis is limited, so that the protective sleeve 3 cannot rotate under the torque of the sleeve cutting knife 2. The protective sleeve 3 may only be moved relative to the grip 1, and may not rotate relative to the grip 1, which can avoid that the protective sleeve 3 is driven to rotate when the sleeve cutting knife 2 rotates, thus preventing damage to the blood vessel by the rotation of the protective sleeve 3.

In some embodiments, as shown in FIG. 5, a top of the fixing sleeve 5 is provided with a guiding groove, and the guiding groove is provided in the shape of a rounded table, and the guiding groove may be configured to guide the guiding wire 26 through the fixing sleeve 5, making it easier for the guiding wire 26 to be inserted into the fixing sleeve 5, so that the fixing sleeve 5 has a guiding function, thereby making it easier to insert the guiding wire 26 into the protective sleeve 3.

Figure 10:
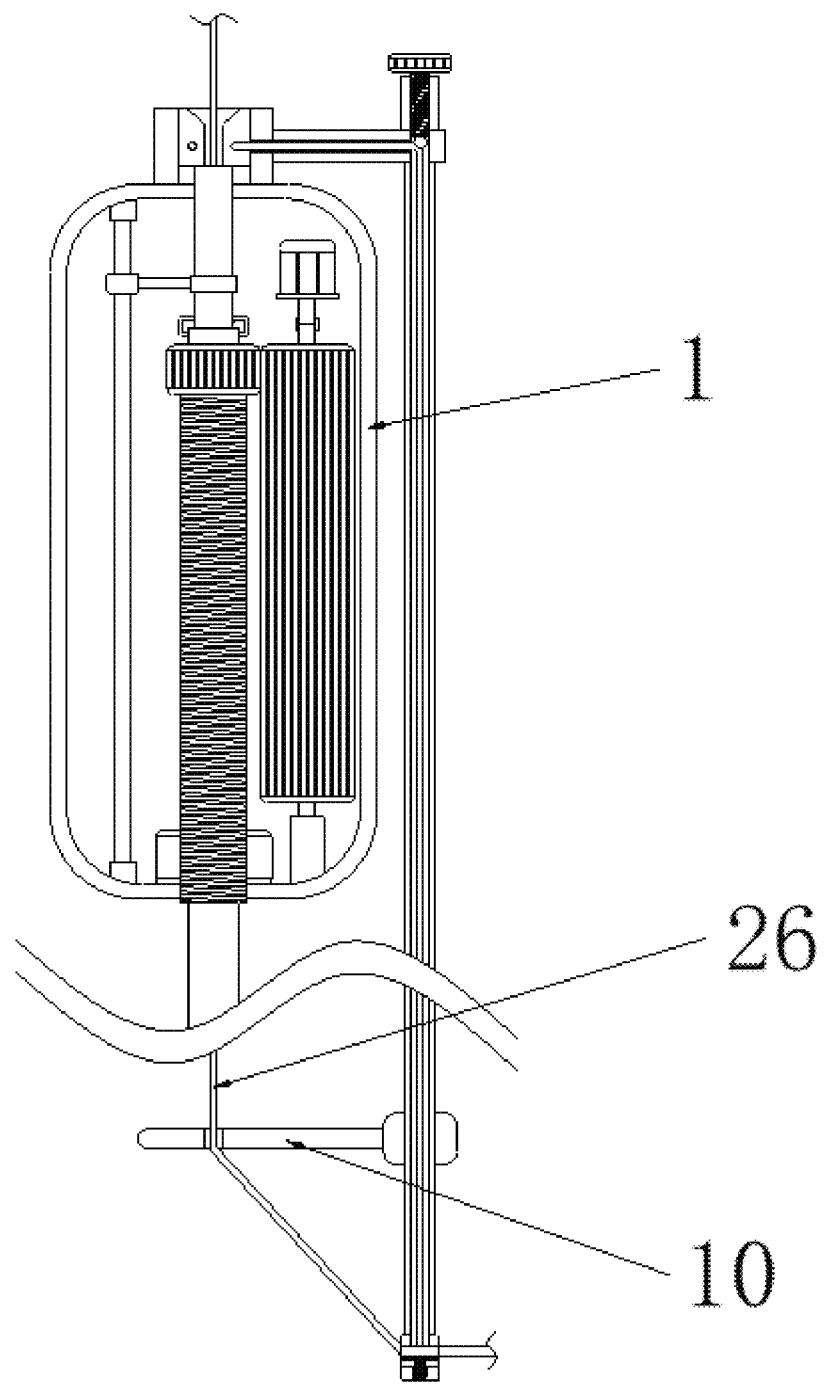
FIG. 10 is a schematic diagram of a cross-sectional structure of a great saphenous vein collection device using a double cannula knife when used in surgery according to some embodiments of the present disclosure.

FIG. 10 is a schematic diagram of a cross-sectional structure of a great saphenous vein collection device using a double cannula knife when used in surgery according to some embodiments of the present disclosure.

In some embodiments, as shown in FIG. 10, the healthcare provider may cut the skin at both ends of the vein to be taken and cut off the vein, retain an end of the vein for ligation, then thread the guiding wire 26 into the fixed sleeve 5, and then thread the guiding wire 26 in from one end of the protective sleeve 3 and out from the other end of the protective sleeve 3. The guiding wire 26 is then threaded into the vein through the skin incision in one place and out through the skin incision in the other place. The end of the guiding wire 26 may pass through the through-hole of the fixing seat 11, the healthcare provider may then rotate the adjusting bolt 17 to cause the adjusting bolt 16 to move in the direction of the spinning out, and as the adjusting bolt 16 spins out, the adjusting bolt 16 may pull the first traction rope 6 to move, thereby causing a loop portion of the first traction rope 6 to pull the fixing sleeve 5 to tighten, causing the inner wall of the fixing sleeve 5 to press against the guiding wire 26, thereby fixing the end of the guiding wire 26. Meanwhile, the adjusting bolt 16 pulls the second traction rope 14 to move when it is screwed out in a direction of screwing out, thereby driving the platen 12 to move, so that the guiding wire 26 is pressed between the platen 12 and a top inner wall of the through hole, thereby providing fixation of the other end of the guiding wire 26. The healthcare worker may then turn on the motor 22, so that an output end of the motor 22 drives the second gear 21 to rotate, and the second gear 21 rotates to drive the first gear 20 to rotate. The first gear 20 rotates to drive the threaded pipe 18 to rotate, and the threaded pipe 18 is threadedly connected to the nut 19 to enable the threaded pipe 18 to move relative to the grip 1, so that drives the sleeve cutting knife 2 to rotate and move relative to the grip 1, which allows the sleeve cutting knife 2 to better cut the tissue, and when cutting the tissue, the blood vessel may be always located inside the protective sleeve 3, thereby protecting the blood vessel and preventing the sleeve cutting knife 2 from cutting the blood vessel.

Some embodiments of the present disclosure provide a great saphenous vein collection device using a double cannula knife, wherein the drive mechanism drives the sleeve cutting knife in a direction away from the grip, so that the sleeve cutting knife is inserted into an interior of the tissues, and the blood vessel is always located in the protective sleeve when cutting the tissues, thereby protecting the blood vessel and preventing the sleeve cutting knife from cutting the blood vessel. The first fixing mechanism is able to fix an end of the guiding wire arranged within the threading cylinder, so that the guiding wire may not move relative to the protective sleeve, thereby enabling the guiding wire to be better positioned for the movement of the sleeve cutting knife, so that the sleeve cutting knife may be better positioned when cutting the tissue, and the sleeve cutting knife moves more accurately when cutting the tissue, further preventing accidental injury to the blood vessel, and through the setting of the first fixing mechanism, the fixation of the guiding wire is more convenient, which reduces the difficulty of the surgical operation and facilitates the use of the guiding wire.

The basic concepts have been described. Obviously, for those skilled in the art, the detailed disclosure may be only an example and may not constitute a limitation to the present disclosure. Although not explicitly stated here, those skilled in the art may make various modifications, improvements, and amendments to the present disclosure. These alterations, improvements, and modifications are intended to be suggested by this disclosure and are within the spirit and scope of the exemplary embodiments of this disclosure.

At last, it should be understood that the embodiments described in the disclosure are used only to illustrate the principles of the embodiments of this application. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A great saphenous vein collection device using a double-sleeve knife, including a grip, a sleeve cutting knife, and a protective sleeve;
    wherein the protective sleeve is provided inside the sleeve cutting knife and the sleeve cutting knife is rotationally connected to the protective sleeve;
    the protective sleeve penetrates through the grip;
    the grip is provided with a drive mechanism for driving the sleeve cutting knife to move relative to the grip;
    a threading cylinder is fixedly arranged at a top of the grip, one end of the protective sleeve extends into an interior of the threading cylinder, a first fixing mechanism for fixing a guiding wire is provided in the interior of the threading cylinder;

a first support rod is fixedly connected to a side wall of the threading cylinder, and a second support rod is fixedly connected to an end of the first support rod;

the second support rod is provided with a second fixing mechanism for fixing the guiding wire at an end of the second support rod away from the first support rod; and a sliding sleeve is slidably arranged on the second support rod, and the sliding sleeve is fixedly connected with a fixing plate; and the fixing plate is provided with a threading hole.

2. The great saphenous vein collection device using the double-sleeve knife of claim 1, wherein the first fixing mechanism includes a fixing sleeve and a first traction rope;

the fixing sleeve is provided in a ring shape, and the fixing sleeve is provided with an annular channel;

the first traction rope is passed within the annular channel; and the first support rod is provided with an adjusting mechanism for pulling the first traction rope.

3. The great saphenous vein collection device using the double-sleeve knife of claim 2, wherein the adjusting mechanism includes an adjusting cylinder;

the adjusting cylinder is arranged on the first support rod, the adjusting cylinder is threaded arranged with an adjusting bolt; and the first traction rope passes through an inner cavity of the first support rod, a bottom end of the adjusting bolt is connected to an end of the first traction rope.

4. The great saphenous vein collection device using the double-sleeve knife of claim 3, wherein the second fixing mechanism includes a fixing seat;

the fixing seat is fixedly arranged on an end of the second support rod away from the first support rod;

the fixing seat is provided with a through-hole, and the through-hole is slidably arranged with a platen;

a tension spring is fixedly connected to a bottom end of the platen, a bottom end of the tension spring is fixedly connected to the fixing seat;

a second traction rope is fixedly connected to a top of the platen; and the second traction rope passes through an inner cavity of the second support rod and a top of the second traction rope is connected to a bottom end of the adjusting bolt.

* * * * *